United States Patent
Sweetser

(10) Patent No.: US 7,653,557 B2
(45) Date of Patent: Jan. 26, 2010

(54) CLIENT DRIVEN HEALTHCARE SYSTEM AND PROCESS

(76) Inventor: Christine B. Sweetser, 902 E. 8th St., Linn Haven, FL (US) 32444

( * ) Notice: Subject to any disclaimer, the term of this patent is extended or adjusted under 35 U.S.C. 154(b) by 0 days.

(21) Appl. No.: 11/315,054

(22) Filed: Dec. 22, 2005

(65) Prior Publication Data
US 2006/0100906 A1    May 11, 2006

Related U.S. Application Data

(63) Continuation of application No. 09/617,476, filed on Jul. 17, 2000, now abandoned.

(51) Int. Cl.
G06F 19/00    (2006.01)
G06Q 40/00    (2006.01)
(52) U.S. Cl. .............................. 705/3; 705/4
(58) Field of Classification Search .................... 705/2, 705/3, 8, 9; 600/300
See application file for complete search history.

(56) References Cited

U.S. PATENT DOCUMENTS

| | | | | |
|---|---|---|---|---|
| 5,072,383 A | * | 12/1991 | Brimm et al. | 705/2 |
| 5,193,855 A | * | 3/1993 | Shamos | 283/117 |
| 5,713,350 A | * | 2/1998 | Yokota et al. | 600/300 |
| 5,748,907 A | * | 5/1998 | Crane | 705/2 |
| 5,961,332 A | * | 10/1999 | Joao | 434/236 |
| 5,974,389 A | * | 10/1999 | Clark et al. | 705/3 |
| 6,208,974 B1 | * | 3/2001 | Campbell et al. | 705/3 |
| 6,283,761 B1 | * | 9/2001 | Joao | 434/236 |

OTHER PUBLICATIONS

Labb, Deborah A, "Definition appropriate care: A matter of perspective" Sep./Oct. 1999; Healthcare Executive, vol. 14 No. 5; p. 12.*

* cited by examiner

Primary Examiner—C Luke Gilligan
Assistant Examiner—Rachel L Porter
(74) Attorney, Agent, or Firm—McNair Law Firm, PA; Cort Flint

(57) ABSTRACT

An advanced primary nurse care system and process is disclosed which is client-driven for processing a number of clients in a timely manner with enhanced healthcare outcomes. The system and process are sized to provide an optimum patient flow and healthcare. The system includes a computer network having a central system computer. A computer program resides on the system computer for creating a real-time client record as the client proceeds through the system and process. There is a client station connected in the computer network where the client record is initially created and accessed on subsequent visits using a unique client ID code. A client station display monitor displays medical questions regarding the client's health state whereupon the client inputs responses to the questions into the client record. A nurse station is connected in the computer network for receiving the client in the healthcare flow for collecting vital signs and other laboratory information. There is a nurse station input device provided for inputting the information into the client record. There is a practitioner station connected in the computer network where the client record is accessed and displayed to a medical practitioner and the client during an examination and consultation. Exam data originating at the practitioner station is input into the client record such as prescriptions and alternative remedies. At the end of the visit, the client leaves with a take-home report compiled from the real-time client record containing the information needed for the client's healthcare.

5 Claims, 5 Drawing Sheets

CLIENT DRIVEN HEALTHCARE SYSTEM AND PROCESS

The application claims the benefit of prior application Ser. No. 09/617,476, filed Jul. 17, 2000 now abandoned, and is a continuation of the prior application.

BACKGROUND OF THE INVENTION

The present invention relates to healthcare, and more particularly to an advanced healthcare system and process wherein multi-step healthcare is primarily driven by the client in a computerized system centered around an interactive, real-time client record to provide better quality healthcare with increased client interaction and access yet with decreased costs.

In the coming years many local healthcare markets are expected to experience even more change as the provider-dominated system loses leverage with managed care penetration. Many local economies are booming with tourism, construction and retail sales. Population growth is steady and projected to increase. Oftentimes in the past, this set of items has been in conflict. The provision of quality healthcare with increased client access and controlled costs is a problem to which considerable attention need be given. There is a need to help educate and produce wise medical consumers so that healthcare consumers and their practitioners can work together to manage health problems and costs.

Prior healthcare systems and processes have employed a client or patient flow wherein various computerized inputs are utilized to facilitate the process. For example, U.S. Pat. No. 5,319,543 discloses a medical record keeping system utilizing a work flow process rather than a central database approach. This system responds to requests from various application programs by routing the defined cases to particular work-queues. This patent does not provide a consumer driven real-time access to patient information and information is processed in queues. U.S. Pat. No. 5,594,638 discloses a system for providing computerized medical diagnosis and treatment advice, commonly referred to as an expert system. The medical advice is provided over a telephone network. The information available to the patient can be updated almost instantly. The system is designed to provide medical advice for approximately 100 common medical problems and to be accessed by non-medical personal. U.S. Pat. No. 5,823,948 discloses a system for tracking of patients and medical records. The system allows for real-time access to the patient's history. Additionally, the system can automatically receive and store information from outside sources, such as X-ray, transcriptions, labs, registration, central supply and the pharmacy. The system is designed to be used by nurses, doctors, and other medical personnel. The system also provides discharge or exit instructions for the patient. U.S. Pat. No. 5,845,253 discloses a method for processing and recording patient data using a handheld computer so that historical information can be maintained. The system uses clinical codes to represent the conditions of the patient. Questions are directed to the user in order to collect information about the patient. Generally, this method seeks to improve the data collected from the patient and to maintain more accurately the medical history. The use of a handheld computer allows the method to be portable while the collected data is transmitted to the traditional desk top at varying intervals. U.S. Pat. No. 5,867,821 discloses a method for distributing and administrating medical services, entertainment services, medical records, and educational material to the patient in an electronic format. Primarily, this system is a information retrieval system for information which has been previously recorded. This system does not concern the method in which the information should be collected. U.S. Pat. No. 5,869,822 discloses a fingerprint identification system used in conjunction with an encoded identification card. When the card is created, the fingerprint is converted into numbers and stored. Subsequent use of the card requires that the fingerprint be taken again, converted to numbers and compared to the fingerprint at the time the card was created. If the numbers match, use of the card is allowed.

Accordingly, an object of the present invention is to provide an integrated healthcare system and process which is primarily client-driven wherein collaborative decisions are made regarding the client's healthcare.

Another object of the invention is to provide an integrated healthcare system and process centered around a real-time client record which is originated by the client on a system computer and accessed at different business and clinical stations for client/practitioner review and input to provide quality healthcare to a flow of clients at reduced costs.

Another object of the present invention is to provide a primarily client-driven healthcare system and process which focuses on the mind, body, and spiritual aspects of care wherein the client is optimally involved. Holistic, complementary healthcare, covering a broad spectrum of integrated therapies, is enjoying a renaissance.

Another object of the present invention is to provide a healthcare system and process having a plurality of clinical stations connected in a central system computer network whereby a real-time client record can be accessed by the client and medical personnel as the client progresses through the system and process and a final take-home report is generated containing all information for the client's care.

SUMMARY OF THE INVENTION

The above objectives are accomplished according to the present invention by providing an advanced, integrated healthcare system and process for processing a number of clients in a client-driven and timely manner through a facility while providing quality healthcare at lower costs which includes a computer network having at least one central system computer with a computer readable medium. A system computer program resides on the system computer which includes instructions embodied in computer readable code for creating a real-time client record stored in a system database as the client is processed through the system. This is the "e" solution that connects data, internet, fax and video communications services for the client.

A plurality of client stations having computer terminals connected in the computer network receive the clients entering the facility. An input device is located at the client station connected to the computer terminal for inputting the client information to originate the client record. The system program includes instructions for soliciting responses to questions regarding the client's health state and generating diagnostic analysis for the client's health state based on the responses. There is a display monitor for displaying the questions at the client station where the client responses to the questions are input into the client record. The client station includes an input identification device for generating a computer readable ID code identifying the client and a respective client record. The various other stations in the system and process include networked ID input devices so that the client record may be accessed from the various stations. Advantageously, the identification device comprises a fingerprint sensor for sensing the finger print of the client as the ID code.

There is at least one nurse station having a computer terminal connected in the computer network for accessing the client record and collecting vital signs and other laboratory information from the client, and a nurse station input for inputting the information into the client record in the form of lab data. Advantageously, the nurse station comprises a plurality of computerized blood analysis machines which include one of a hematology machine, blood pressure, pulse and temperature, i.e. "vital signs" machine, and blood chemistry analyses machine connected directly to the system computer for direct input of the lab data. There is a practitioner station at which a number of medical practitioners may be stationed for receiving the clients. Preferably, one or more practitioner stations include a computer terminal connected in the computer network for accessing the client record and a display monitor for displaying the client record. The practitioners and the client can access the computer terminal in the examination room/station during the examination for collaborative decisions. A station input device is provided for inputting exam data into the client record from the examination and consultation. Alternate therapy stations may also be provided where the client may review alternate therapy options and consult with practitioners licensed in alternative and complementary therapies. A computer terminal is connected to the system computer for generating options data representing recommended therapies, including alternative naturopathic, acupuncture, chiropractic, massage, and nutritional therapies for input into the client record. At the end of the visit, a printed, take-home report is compiled based on the client record by the system computer upon termination of the client process in the facility for the client to take home.

A first time client is welcomed to the center by a facilitator who directs and assists the client to the client station. A first time client enters biographic and demographic information via a "touch screen" input device into the computer. Preferably, the client's fingerprint is input as an identification code to identify the client in later visits. When directed to do so on subsequent visits, the client places their finger into the sensor for instant identification, record access and recall. After inputting the fingerprint identification, the client is prompted to enter, by touch screen, the reasons for the visit, symptoms, complaints, and upgraded status of condition and history. The client then proceeds to a triage nurse station where fingerprint identification brings up the client's records of his visit reason complaint, health screening and promotional package selection, etc. Information regarding the selection of services made earlier is available real-time in the computer. At the nurse station, vital signs and laboratory test specimens are gathered and processed. The nurse station results are electronically downloaded to the client record in the system database. The client then progresses to the practitioner station where private consultation and examination are conducted with an allopathic or, if chosen, an alternative healthcare practitioner. The real-time client record is brought to the screen by fingerprint identification at the practitioner station. The client record, current concerns, symptoms and/or complaints; and the triage results are reviewed by both the practitioner and client and discussed. Collaborative decisions, specific to the client's complaint, are made while viewing clinical data and the real-time client record on line. Decisions are made based on suggested medical guidelines and practice parameters available through the system computer program. Material from the medical database program pertinent to the client's clinical educational information needs is printed for a client take home folder. Prescriptions are entered into the client record and printed or electronically transmitted to the client's preferred pharmacy. Based on collaborative decisions between the client and practitioner, clinical and/or complementary alternate therapy options are reviewed. The clinical and alternative therapy options are reviewed, recommended, and documented in the real-time client record; and selected and administered in the center, or client-instructed for home use. Herbal, vitamin, and nutraceutical supplement choices, based on recommendations and mutual decisions are entered into the client record database when purchased from the center's herbal emporium station. The client leaves the center with a folder of information regarding his current visit. During future visits the client accesses the client record with the electronic fingerprint sensor and immediately updates and enters current data into the computer.

DESCRIPTION OF THE DRAWINGS

The construction designed to carry out the invention will hereinafter be described, together with other features thereof.

The invention will be more readily understood from a reading of the following specification and by reference to the accompanying drawings forming a part thereof, wherein an example of the invention is shown and wherein.

DESCRIPTION OF A PREFERRED EMBODIMENT

Figure 1:
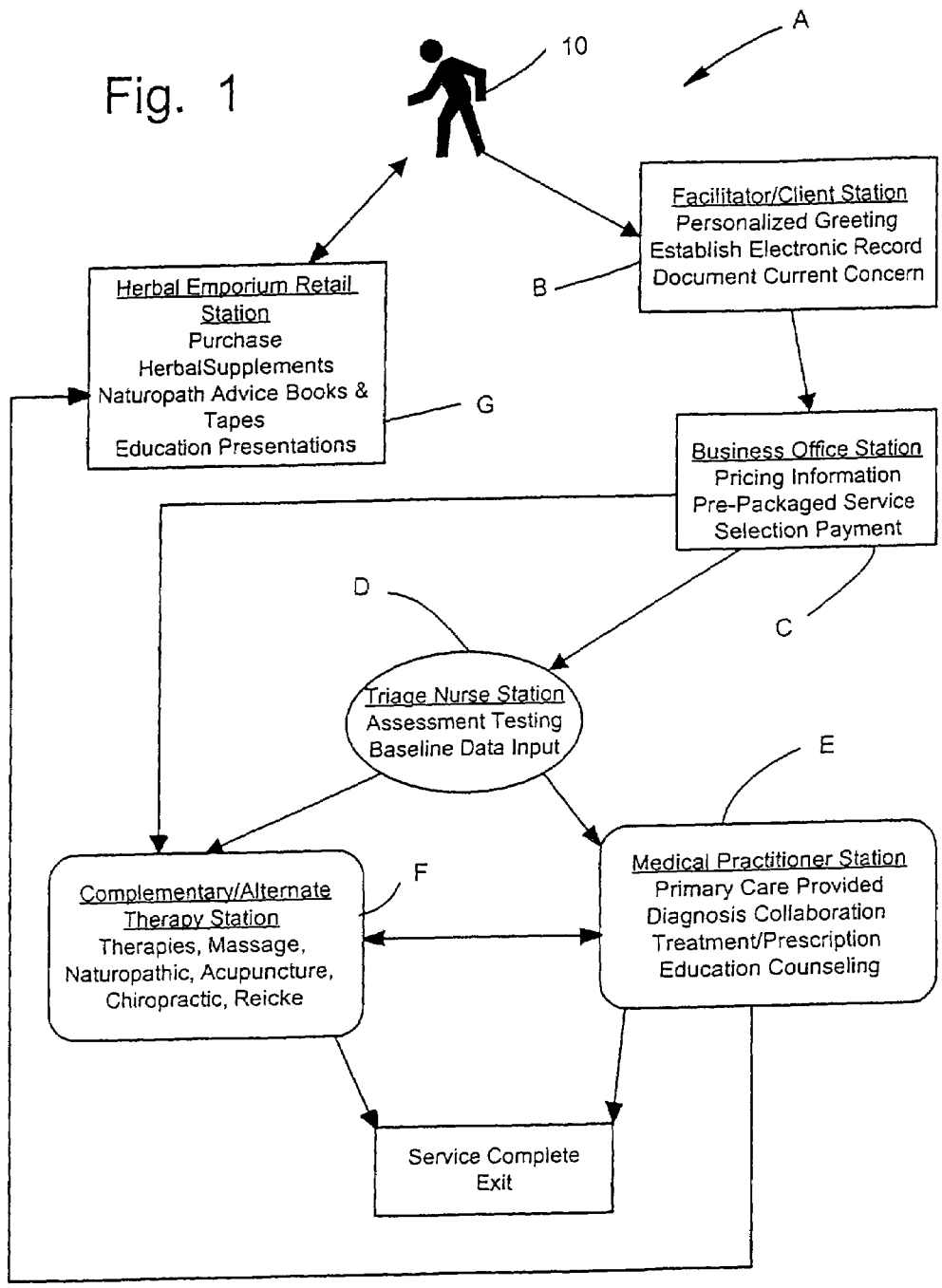
FIG. 1 is a schematic diagram of an advanced client-driven healthcare system and process according to the invention.

Referring now to the drawings, the invention will now be described in more detail. Referring to FIG. 1, an advanced healthcare system and process, designated generally as A, is illustrated for processing a number of clients through a facility in a client-driven manner, generally without waiting. The healthcare system and process includes a client station, designated generally as B; a business office station, designated generally as C; a clinical triage nurse station, designated generally as D; and a clinical medical practitioner station, designated generally as E. Preferably, there is also an alternate therapy station, designated generally as F, and an emporium station, designated generally as G.

In accordance with the system and process, a client 10 enters the facility, and is directed to a client station B. A facilitator (not shown) may be provided to direct and assist the client at the station. As can best be seen in FIG. 2, client station B includes a computer terminal 14 having an input device 14a and display monitor 14b. At station B the client receives a personalized greeting and begins the creation of a real-time, electronic client record 12 by way of input device 14a. The information input by the client is compiled into client record 12 and stored in a computer readable database of a system computer 16 by means of a computer program 18, to be described in more detail. There may be a number of client stations B, depending on the desired client flow sizing. In the illustrated embodiment, designed for processing twelve clients simultaneously, there are three client modules 15, each having four client stations B. An auxiliary identification (ID)

input device 20 is located at each client station B for inputting a client identification code into client record 12. ID input devices 20 are also provided at the stations described below for accessing or retrieving client record 12. Client input device 14a is preferably provided in the form of a touch screen input for client convenience. Alternatively, a keyboard input may be used.

System computer program 18, residing on system computer 16, preferably includes practice management software 18a integrated with medical diagnostic software 18b which create a real-time client record 12 stored in the system database. System medical-diagnostic software 18b prompts the client with queries or questions that require "yes" or "no" responses, or a selection from a multiple-choice drop down list. The system software prompts the client into responses regarding reasons, symptomatology, complaints, etc. Advantageously, the client identification input device is provided in the form of a fingerprint sensor device 20. Sensor 20 generates a unique ID code 20a for the client and avoids the problem of a client losing an ID card or forgetting an ID password. A first time client enters biographic and demographic data at client station B. The client originates client record 12 by inserting an index finger or thumb into sensory device 20 to identify and verify data recording. When revisiting the center, clients will be able to access their records by a fingerprint identification device. Clients may also register in advance of coming to the center at the center's web site on the Internet. The web site may be provided with confidentiality and security safeguards; and access to personal records may be by password. On line registrant users may keypunch data and be assigned a password for future access. Use of the Internet further enhances the center's service capabilities integrating communications and connecting customers to build relationships and continuity of care. When visiting the center, pre-registered online clients will be able to access their records by fingerprint I.D. technology. The facilitator assists clients who are unfamiliar with the facilities. A detailed client history is obtained without taking any of the medical staffs time. Client data 22 input into client record 12 from client station B includes fingerprint ID code 20a, biographic data 22a, demographic data 22b, and symptoms and complaints data 22c (FIG. 3a). After the initial visit, the biographic and demographic data will be in the permanent record and the client may only be prompted for the visit reason, symptomatology, current complaint, etc. Touch screen interactive responses to the system computer program queries eliminates waiting room time, streamlines registration to a single input process, and is totally client driven.

Any suitable medical-diagnostic program 18b may be utilized such as Prime Care™ medical software available from Prime Care Systems Inc. of Newport News, Va., which fully integrates with Zygote™ practice management software 18a available from Populus Systems, Inc. of St. Petersburg, Fla. Programs 18a and 18b are designed to interface with each other, and it has been found that the integrated programs provide an advantageous software system 18 for the present system and process. The Prime Care software uses an authoritative and comprehensive knowledge bank of 285 symptom and problem-oriented client history questionnaires collectively containing over 100,000 chief complaints and disease state questions. Clients at client station B are seated at computer terminals 14 and answer complaint-specific questions by using just the number keys to indicate answers that apply to them, or touch screen "yes" or "no" answers. No typing or computer skills are required. The software may be fully integrated and synergetic with all electronic devices employed in the system and process. Medical software 18a may be customized and mapped for each network computer and electronic device at nurse station D and practitioner station E, and allows accurate directional exchange of data between client record 12 and management software 18b.

At business station C, insurance and other business and service information is input in the form of business data 24. Business data 24 includes ID code 20a, insurance information 24a, health package purchases 24b, and payments 24c. Business station C includes at least one computer terminal 23 having an input device 23a and a monitor 23b. The computer program directs the client to progress from the reception area to a business office station where his insurance card is scanned and placed into the client record on the system's database. Depending upon the client's responses to the computer query, the level of the visit and services are established. Prepackaged or special promotion services may be selected; charges are determined, and money is collected and posted to the client's account.

Figure 3:
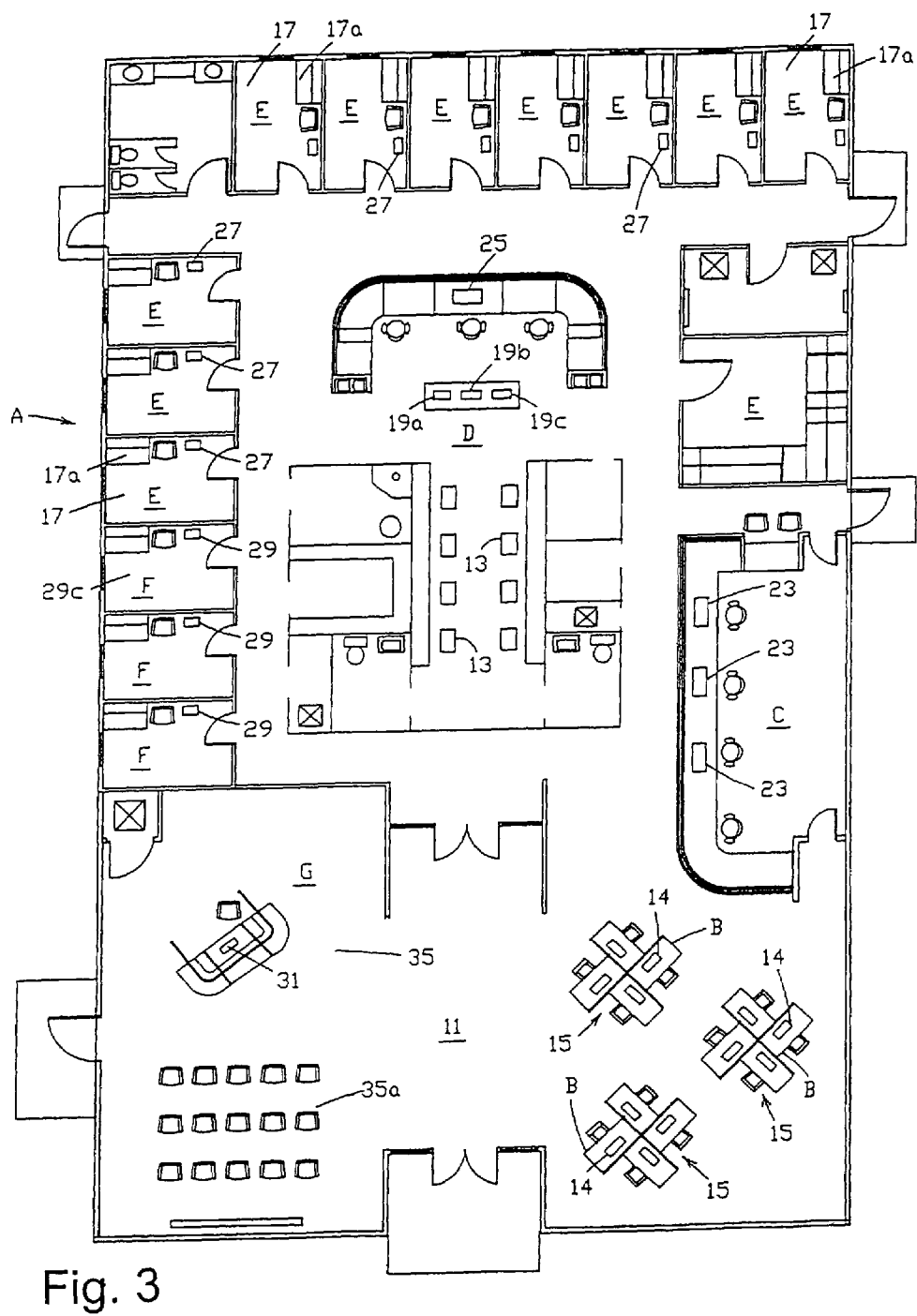
FIG. 3 is an operational floor plan of an exemplary embodiment of a healthcare system and process according to the invention.
Figure 3A:
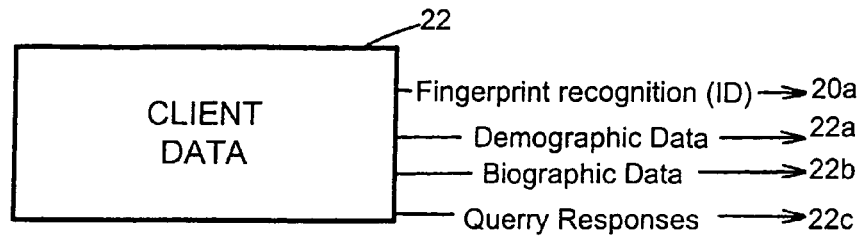
FIGS. 3a-3f illustrate block diagrams of data input from the various client, business, and clinical stations according to the invention; and, FIG. 4 is a flow diagram of a system and process according to the invention.
Figure 3B:
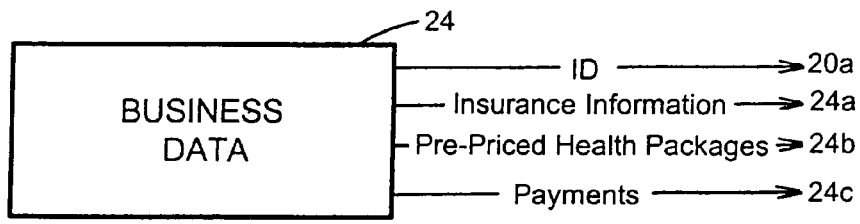
Figure 3C:
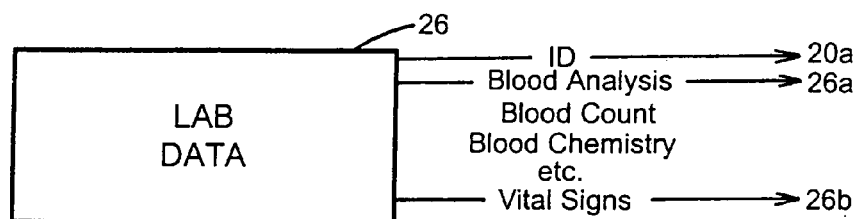
Figure 3D:
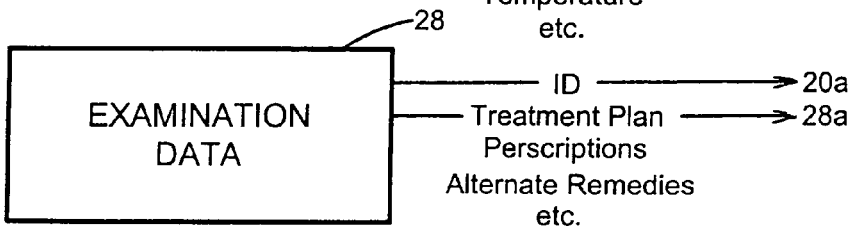
Figure 3E:
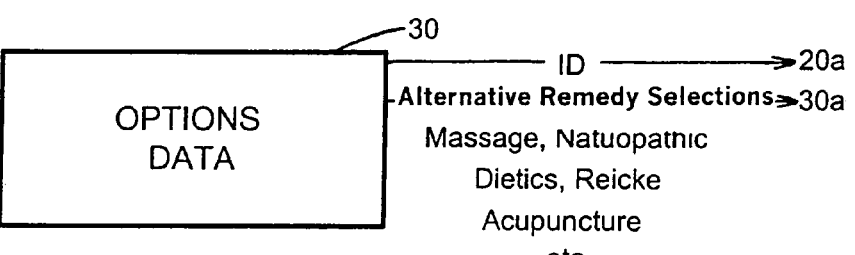
Figure 3F:
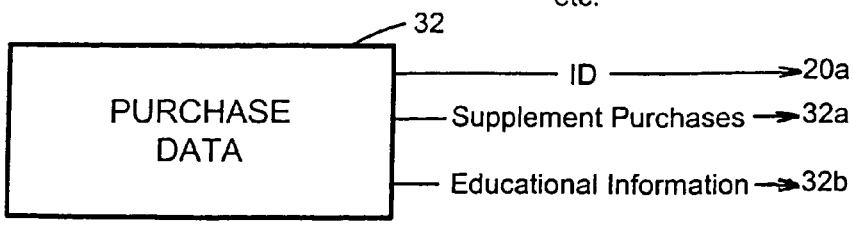

As can best be seen in FIG. 3, nurse station D includes at least one computer terminal 25 having an input device 25a and a display monitor 25b. Needed specimens and vital signs data are collected at the nurse station and analyzed in the form of lab data 26. Lab data 26 is then directly downloaded into client record 12. There are a number of client blood-drawing desks 13 at nurse station D where blood samples may be drawn from the client for analysis by computer instruments and the like. The results of the blood analysis are input as 26a directly into the identified client record 12 as part of lab data 26. For example, there may be a computerized hematology machine at 19a for generating blood count information, a computerized blood chemistry analyzer at 19b for generating sodium, potassium, glucose, and lipids information from the client samples which is input at 26b, and a computerized blood pressure, temperature and pulse machine at 19c for inputting the client's vital signs information at 26c, as well as any other machines as desired. A suitable computerized hematology analyzer is available from Beckman Coulter of Fullerton, Calif. A suitable computerized blood chemistry analyzer machine is available from Roche of Indianapolis, Ind. A suitable computerized blood pressure, temperature and pulse machine is available from Welch/Allyn of Skaneateles Falls, N.Y. Computer terminal 25 is located at a conventional nurse desk 19d for manual input of lab data and client ID.

As can best be seen in FIG. 3, a plurality of practitioner stations E are preferably provided, each of which includes a computer terminal 27 having an input device 27a, and a display monitor 27b. At practitioner station E, exam data 28 is originated by a medical practitioner (not shown) and the client. Exam data 28 includes client ID code 20a, and may include treatment plan data 28a such as prescriptions, alternative remedies, etc. The data is automatically input into client record 12 via input device 27a. Practitioner stations E may be located in private examination rooms 17 having examination tables 17a. Additionally, a practitioner office E may be provided for the practitioners not seeing clients. Preferably there are ten practitioner stations E in the illustrated embodiment.

Alternative therapy station F includes at least one computer terminal 29 networked with system computer 16 having an input device 29a and monitor 29b (FIG. 3). In the illustrated embodiment, there are three alternate therapy stations F located in private rooms 29c. Following the assessment at nurse station D, the client is routed to one or both of the practitioner station E or alternative therapy station F. Any alternative therapy options are input at station F as option data 30 into client record 12. At alternative therapy station F, various options to conventional medical treatment are discussed, such as naturopathic, homeopathic, chiropractic, acupuncture, massage, reicke, dietetic, and other alternative remedies. The alternative therapy or remedy choices 30a are input with option data 30 into client record 12.

Figure 2:
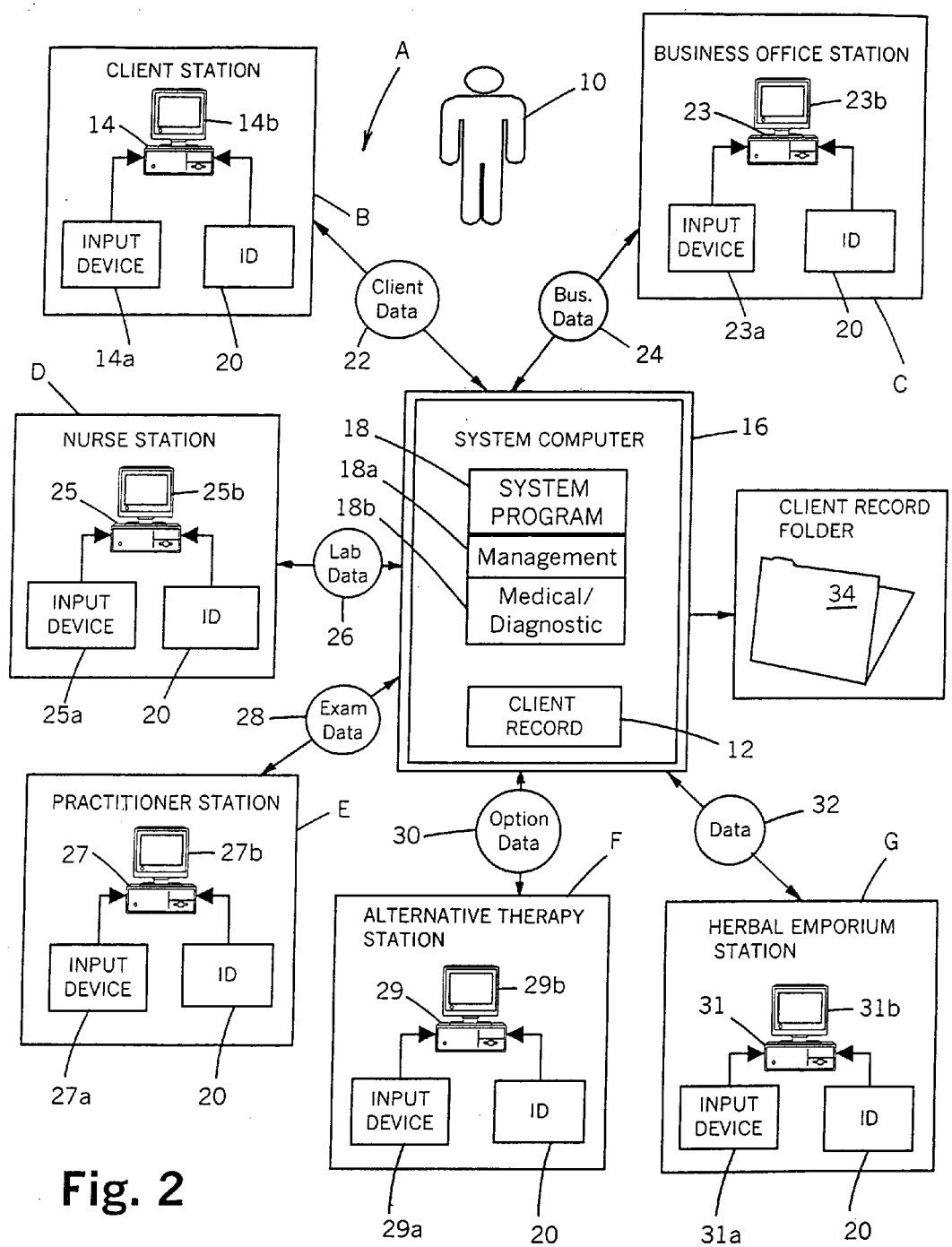
FIG. 2 is a diagram of the system and process hardware and software, and formation of a real-time client record according to the invention.

Herbal emporium station G is where the client may go to for the purpose of purchasing health supplements or educational material with, or without, going through the remainder of the system (FIG. 3). Emporium station G includes a retail section 35 and an auditorium 35a where educational videos may be viewed, and programs held. Emporium station G includes at least one computer terminal 31 networked with system computer 16 having an input device 31a and a monitor 31b (FIG. 2). Client purchase data 32 representing nutrition supplements 32a and educational information 32b purchased at station G is input into client record 12. At emporium station G, herbal, vitamin, nutraceutical, and the like, supplement choices based on recommendations and mutual decisions, can be purchased. All purchases are input as part of the client record 12 using computer input device 31a and ID device 20. The herbal emporium has ongoing educational programming via satellite telecast. Clients may wish to visit the center solely to purchase health supplement supplies, or to view a specific health topic of interest. At the client's direction, any purchases can be entered into their clinical record to document and complete their profile of therapies for future collaborative discussion with professional practitioners. At future consultative visits, fingerprint technology allows access to the client controlled record for immediate update and current data entry.

A highly effective, client-driven healthcare service can be experienced according to the invention where the client (patient) and medical professionals collaborate at individual stations to arrive at a joint decision regarding healthcare status and recommended interventions, with the information automatically compiled into a real-time client record. From completion of the computer interactive registration, the client proceeds, without waiting, to business station C and the clinical stations D, E, F, and G of their choosing. The clinical stations are for primary healthcare and treatment combinations of alternative and complementary interventions as selected by the client. Data is captured at each station and flows through the computer network to compile client record 12. As data is recorded, the level of visit and service is established. Promotional, prepriced packages of services are available for health screening, health maintenance and illness prevention choices by the client.

Operation

Figure 4:
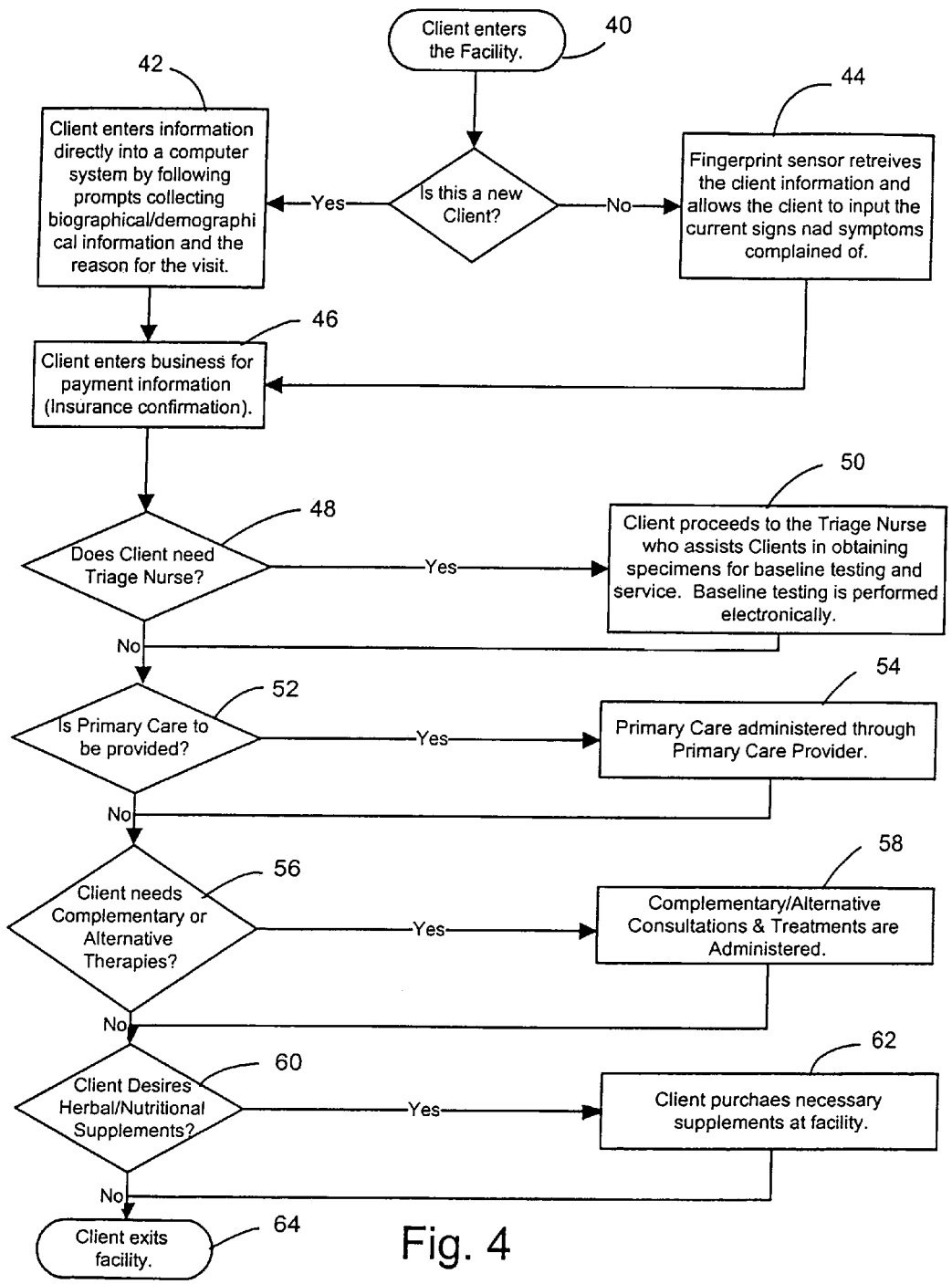

The operation of a system and process according to the invention will now be described, referring to FIG. 4. A facilitator greets the client upon entrance at 40, and welcomes and directs the client in the reception area of facility 11 to a computerized client station B for entry of client data into client record 12. If the client is a new client, then a new client record 12 is originated at 42. If the client is a previous client, then the existing client record is retrieved at 44 by utilizing the fingerprint sensor ID device. In either case, after completion of inputting client data 22, the client proceeds to the business office to input any needed business data 24 or selection of prepriced medical packages, such as health screening, health maintenance, and illness prevention choices by the client at 46. Also, a decision is made at 46 as to whether the client needs a triage nurse. If so, the client proceeds at 50 to the triage nurse station D where the client is assisted by the triage nurse in obtaining the needed specimens for testing services. The testing results including the client's vital signs, specimen analysis, and laboratory information are input as lab data 26 into client report 12 for a practitioner to review when examining the client. The report contains the client's current problems, medications and allergies, all positive and significant negative subjective responses, vital signs and a list of the diagnostic considerations triggered by the client's responses input in the form of client data 22 into client report 12. Next, a decision is made at 52 as to whether primary care is needed. If so, the client proceeds at 54 to a primary care practitioner station E. At practitioner station E, client report 12 is accessed and reviewed by an advanced practice nurse, primary care M.D., or other licensed practitioner (not shown) when consulting with the client about their reason for the visit. The computer program practice guidelines and clinical parameter data base significantly reduces the possibility of a practitioner failing to consider a diagnostic possibility, thereby standardizing and greatly improving the quality of client care. During clinical consultation and examination at practitioner station E, the client's real-time record 12 is displayed for both the practitioner and client to review. The current visit reason, triage lab documentation and potential differential diagnoses are available, as well as the facility's complete historical health record of the client. The client record may include any other health records the client may wish to scan into the record from other facilities as integration of other providers' records enhances the continuity and quality of care for clients. Both client and practitioner review the physical findings, clinical profiles, differential diagnoses, and then collaboratively discuss and decide on a treatment specific to the client's reason for the visit and chief complaint. Based on collaborative decisions, allopathic, complementary, and alternative treatments are selected by the client, and administered in the center, or the client is instructed in home use. Medical guidelines and practice parameters are integral to the medical diagnostic software 18b. The differential diagnosis and cascading of questions is driven by an in-depth, thoroughly researched, and continuously updated medical university program data base (18b). The practitioner documents physical findings and assessments, inputs a treatment plan, prescribes medication, and disseminates client educational materials. The practitioner station information is input into the record as exam data 28. If it is determined that the client needs alternative therapy at 56, the client is directed to alternative therapy station F at process step 58 where the client's needs are assessed and downloaded as data 30 into the client record 12. Likewise, at 60 a decision is made as to whether the client needs herbal, vitamin, or nutritional supplements. If so, the client proceeds in the flow to emporium station G where the client's record is accessed and any needs of the client assessed, recorded and downloaded as option data 32 into record 12. The client then exits the process flow, system, and facility at 64.

The client exits with pertinent material, such as prescriptions, drug data sheets, diagnosis, educational information, treatment instructional information, and insurance claim forms printed real time in the client's take home report and folder 34. The report is a hard copy document for client use and review. Prescription data can also be electronically transmitted to the client's off site pharmacy. At each decision point 46, 48, 52, 56, and 60, collorative decisions are made driven by the client with the assistance of qualified health personnel.

Thus, it can be seen that a highly advantageous, primary care practitioner system and process can be had according to the present invention designed to provide a service that meets a major challenge in healthcare delivery. The challenge of harnessing the electronic medical record with client controlled access and collaboration that is real-time in function, feed back and intervention. The model provides maximized service and satisfaction in primary healthcare delivery.

By using system program 18 and answering the "yes" or "no" questions, a detailed medical report is generated containing the client's responses and a list of diagnostic possibilities triggered by those responses. The client is allowed to answer questions about their medical condition at their own pace which allows for more accurate straightforward answers. The medical staff does not spend time compiling medical history questions and responses; allowing the system of the present invention to process a number of clients in a flow-through system in less time than it would ordinarily take to see a physician and without sacrificing quality of care. By using fingerprint sensor 20, at each of the stations in the system, reliable access is had to the client record throughout the client's visit to the center. It allows clinical, financial, specimen test, or retail purchase data to be viewed, reviewed and updated at any station, or at any point should the client and healthcare practitioner need it. On return visits to the center, instant recall by fingerprint identification again eliminates client waiting time as the program queries the client as to reason for visit; symptomatology; updated status of condition and history; complaints such as pain, shortness of breath, cough, etc.; and updated demographic information. Client computer record 12 is utilized at each encounter throughout the center as the client progresses from reception through to the business office, then to triage, clinical examination areas, complementary/alternative therapies, and/or retail areas.

The objective of client-driven, quality healthcare at controlled costs is accomplished according to the present invention by providing primary healthcare centers which can be marketed directly to employers and employer coalitions, as well as individual clients, thereby cutting administrative overhead, and "right sizing" the primary care encounter. The traditional medical model is replaced with an expanded client-driven service model. In the client-driven service model, chronic diseases, which account for the majority of medical costs, will be targeted and focused into maintenance schemas using practice guidelines applied across the continuum of care. The objectives of improved quality, increased access, and controlled costs are achieved by the delivery of healthcare services through an integrated system as described in the model. The healthcare consumer will be provided with a "just in time" service.

The traditional existing service care model is changed into a holistic care model of healthcare service in which the consumer is empowered in a client demand-driven system. A need exists for the development of this model by which common care principles from both allopathic and complementary care can be integrated with the power of computers and the Internet to result in improved healthcare for people. The system provides for the consumer and practitioner to work in partnership, share in every medical decision, and become skilled in obtaining the care needed to obtain the desired outcome. The role of primary care providers and mid-level healthcare personnel is enhanced by networking information technology with all facets of healthcare service, including speciality providers and payors. These are the keys to gaining control over the quality and the cost of healthcare. The ultimate outcome is improved client health at a lower cost.

While a preferred embodiment of the invention has been described using specific terms, such description is for illustrative purposes only, and it is to be understood that changes and variations may be made without departing from the spirit or scope of the following claims.

What is claimed is:

1. A client-driven computerized healthcare process performed within a healthcare facility for providing efficient healthcare driven by a real-time client record containing client choices including client choices resulting from collaboration between the client and facility personnel input into the client record in real-time at a plurality of healthcare stations within the healthcare facility, said healthcare facility having at least one individual client station, at least one business station, at least one nurse station, and at least one practitioner station, and a computer network having a plurality of computer terminals located at said stations in communication with a central system computer, wherein said computerized client-driven healthcare process comprises:

a. storing a plurality of individual client records on a computer readable memory;

b. providing a computer readable program residing in a computer memory accessible by said clients and facility personnel from said computer terminals including a medical-diagnostic component having query instructions for initially soliciting client responses to a series of questions concerning the client's condition and symptoms and treatment instructions for processing the client responses to generate diagnostic data containing one or more possible diagnoses;

c. accessing said program on said central system computer directly by a client via said computer terminal at a client station to perform one of originating a client I.D. code and record by a new client and accessing a client record with an existing client I.D. code for the input of client information regarding the current visit;

d. displaying a series of diagnostic questions on a computer terminal at said client station in a form prompting one of a simplified "yes" or "no" response and a response from a multiple-choice drop down list, and inputting said diagnostic question responses directly by said client into said client record at said client station in a simplified manner without the need of assistance of medical personnel at the client station whereby a number of clients can be processed through the client station without assistance in a highly efficient manner;

e. processing said diagnostic responses and generating client diagnostic data containing one or more possible diagnoses of the client's condition, and compiling the diagnostic data as client information in said client record;

f. determining the level of the services needed by the client during the visit by processing the client information including medical question responses and diagnostic data contained in the client record;

g. providing a number of choices for pre-priced healthcare service packages available to the client containing different types of services that may be rendered to the client during the visit to meet their client's medical needs based on the level of services determined for the client;

h. accessing the client record on a computer terminal at said business station in response to inputting said client ID code, displaying said pre-priced healthcare packages for review and selection by the client at said business station, and selecting one of the healthcare packages by said client prescribing the services to be rendered to the client during the visit;

i. compiling business information, including the selected healthcare package into said client record, and the client proceeding at the client's choice to one of a triage nurse station, practitioner station, and facility exit depending on the selected healthcare package;

j. accessing the current client record by the client in real-time on a computer terminal at said nurse station in response to the input of said client ID code for review by a triage nurse and said client, and collecting one or more of said client's specimens, vital signs, and laboratory information as lab data at said nurse station depending on the selected healthcare package, k. determining medical priorities for the client's health treatment by collaboration with said client and said triage nurse at said nurse station based on said diagnostic data, selected healthcare package, and lab data, and compiling said medical priorities in said current client record at said nurse station, whereupon said client proceeds to one of a practitioner station, another healthcare station, and a facility exit depending on the client's choice following collaboration between said client and said triage nurse;

l. accessing said current client record on a computer terminal at said medical practitioner station in response to the input of the client ID code for review by a medical practitioner and said client;

m. originating a treatment plan at the medical practitioner station including one of a treatment for the client's condition, a prescription, and an alternative therapy based on collaborative decisions of the client and medical practitioner upon reviewing the current client record, including the diagnostic data and lab data and any practitioner physical findings at the practitioner station, and compiling the treatment plan into the current client record, whereupon the client proceeds to one of another healthcare station and a facility exit;

whereby an interactive healthcare system is provided based on real-time client and facility personnel collaboration and input to establish a client record of the client's visit for the client's treatment to provide controlled cost and quality healthcare.

2. The process of claim 1 including reviewing alternative therapy options at an alternative therapy station for generating options data representing recommended alternative therapies including one of naturopathic, acupuncture, chiropractic, massage, and dietetic remedies, and inputting said options data into said client record in real-time.

3. The process of claim 1 including drawing client blood samples, analyzing the blood samples taken from the clients, and inputting the results of the analyses of the samples into said client record.

4. The process of claim 1 including reading a fingerprint of the client as said client ID code at said client station, nurse station, and practitioner station.

5. The process of claim 1 including accessing said client record at an emporium station for the purchase of health supplements so that collaborative purchase decisions may be made while reviewing the client record, and said program instructions include instructions for inputting purchase data into said client record at said emporium station.

* * * * *